United States Patent
Seppälä et al.

(10) Patent No.: US 8,129,478 B2
(45) Date of Patent: Mar. 6, 2012

(54) POLYESTER ANHYDRIDE-BASED BIOPOLYMERS

(75) Inventors: Jukka Seppälä, Helsinki (FI); Risto Hakala, Helsinki (FI); Harri Korhonen, Espoo (FI)

(73) Assignee: JVS-Polymers Oy, Espoo (FI)

( * ) Notice: Subject to any disclaimer, the term of this patent is extended or adjusted under 35 U.S.C. 154(b) by 79 days.

(21) Appl. No.: 12/223,284

(22) PCT Filed: Jan. 26, 2007

(86) PCT No.: PCT/FI2007/050042
§ 371 (c)(1),
(2), (4) Date: Sep. 2, 2008

(87) PCT Pub. No.: WO2007/085702
PCT Pub. Date: Aug. 2, 2007

(65) Prior Publication Data
US 2009/0176943 A1    Jul. 9, 2009

(30) Foreign Application Priority Data
Jan. 26, 2006  (FI) ..................................... 20060077

(51) Int. Cl.
*C08G 63/00*  (2006.01)
*C08G 59/00*  (2006.01)

(52) U.S. Cl. .......... 525/437; 424/423; 424/425; 525/89; 528/271; 528/272; 528/306; 528/310; 528/317.1; 528/319; 604/500; 604/527

(58) Field of Classification Search .................. 424/423, 424/425; 525/89; 528/271, 272, 306, 310, 528/317.1, 319; 604/500, 527
See application file for complete search history.

(56) References Cited

U.S. PATENT DOCUMENTS

| | | | |
|---|---|---|---|
| 5,756,652 A * | 5/1998 | Storey et al. .................. | 528/361 |
| 5,925,726 A * | 7/1999 | Seppala et al. ................ | 528/271 |
| 6,774,203 B1 * | 8/2004 | Fukute .......................... | 528/176 |
| 2003/0050432 A1 * | 3/2003 | Ramesh et al. ............... | 528/354 |

OTHER PUBLICATIONS

Synthesis of Poly(ester-anhydrides) Based on Different Polyester Precursors; Silvaniak et al. Biomacromelecules, 2002, 3, 754.*
R. Silvaniak and A.J. Domb et al. ;Biomacromolecules:Volume and Issue Number: vol. 3 p. 754-760, 2002.*

* cited by examiner

*Primary Examiner* — Terressa Boykin
(74) *Attorney, Agent, or Firm* — Kubovcik & Kubovcik

(57) ABSTRACT

Biodegradable polymers formed from biodegradable polyester-based prepolymers, to which ring-structured anhydrides which have different hydrophobicities have been connected, and which are either coupled to form linear thermoplastic polyester anhydrides or cross-linked to form network-structured polyester anhydrides. It is possible to adjust widely the degradation rate and mechanism of the polymers and thus they can be used, for example, in the controlled dosing of pharmaceutical ingredients, for tissue technological applications, in surgery and in bioactive composites.

6 Claims, 4 Drawing Sheets

POLYESTER ANHYDRIDE-BASED BIOPOLYMERS

This application is a 371 of international application PCT/FI2007/050042 filed Jan. 26, 2007, which claims priority based on Finnish patent application No. 20060077 filed Jan. 26, 2006, which is incorporated herein by reference.

BACKGROUND OF THE INVENTION

The present invention relates to new polyester anhydride-based biopolymers and the production thereof.

Polylactide, polyglycol and poly($\epsilon$-caprolactone) are biodegradable polyesters, the use of which in medical applications has been studied extensively. Polyanhydrides, in turn, are one of the most promising materials for pharmaceutical ingredients requiring controlled release because, being sufficiently hydrophobic, they degrade through surface degradation. The polyester anhydrides comprise a combination of these two types of polymers and, as a result, new types of polymeric properties are generated which cannot be achieved with either of the polymers alone.

The most important group of biodegradable plastics comprises aliphatic polyesters, the biodegradation of which is largely based on hydrolysable ester bonds. Aliphatic biodegradable polyesters include polyglycolide, polyactide and polycaprolactone, and notably polyhydroxy butyrate and polyhydroxy valerate, which are produced with the help of microbes. Generally, polyesters are prepared from hydroxy acids or from diacid and diol. To ensure that the aliphatic polyesters have adequate mechanical properties, their molar masses have to be high. The most common means to achieve a high molar mass is to prepare the polyester by a ring-opening polymerisation of lactones. Because the aliphatic polyesters are non-toxic, biocompatible materials, they are often used in the fields of orthopaedics, odontology, pharmacy and surgery.

The aliphatic polyesters degrade through bulk-degradation, consequently, when the hydrolytic degradation of the polymer chains has advanced enough, the pieces lose their mechanical properties and the mass loss begins. If, at this stage, there are still large percentages of pharmaceutical ingredients in the preparation, it is possible that detrimental percentages may be released from it in an uncontrolled manner. In surgical applications, it is not advantageous that the mechanical properties collapse suddenly. By using surface-degradable polymers (polyanhydrides and polyorthoesters), it is possible to achieve a constant zero-order release (i.e. the release is time linear) when the polymers are dissolved from the surface and release the pharmaceutical molecules as the degradation advances.

A special property of the polyanhydrides is that it is possible to make them surface-degradable.

The most important application of the polyanhydrides are the systems of releasing of pharmaceutical ingredients, because the release of pharmaceutical ingredients from surface-degradable polymers is more uniform than from polymers which are degraded by mass-erosion. A condition for the surface-degradation of the polyanhydrides is that the polymer is sufficiently hydrophobic. In this case, water cannot penetrate into the polymer and a hydrolysis must take place only in the surface of the polymer. By using different hydrophilic and hydrophobic monomers, it is possible to adjust the total degradation time of the polymer to range from a few days to several years. Typically, aliphatic dicarboxylic acids are used as the hydrophilic monomers and, correspondingly, either aromatic dicarboxylic acids or different fatty acids are used as the hydrophobic monomers. Gliadel®, which is a polyanhydride-implant comprising carmustine (a cytostatic) and which is used in the post-treatment of cerebral tumours, is an example of the use of polyanhydrides in applications of controlled pharmaceutical dosing. The problem with the polyanhydrides is their sensitivity to the humidity of the air and, because of this, they have to be stored and transported in sub-zero temperatures, which, in turn, is logistically expensive and impractical. Another problem is the brittleness of the polyanhydrides, which makes it difficult to handle them for instance during the surgical installation of an implant.

In order to combine the good mechanical properties of the polyesters and the advantageous degradation behaviour of the polyanhydrides, different polyester anhydrides have been produced. Slivniak and Domb synthesized the ABA copolymer, which comprises a sebacine acid polyanhydride in the middle and polylactic acid blocks at the ends. The polylactic acid blocks were reported to have a substantial effect on the degradation of the polymer and on the release of the pharmaceutical ingredient (R. Silvaniak, A. J. Domb, *Biomacromolecules*, 2002, 3, 754). Xiao and Zhu prepared polycarbonates which comprised anhydride bonds in their main chain. By using sebacine acid as a comonomer, a copolymer was generated, the degradation behaviour of which was reported to be close to surface degradable materials (C. Xiao, K. J. Zhu, *Macromol. Rapid. Commun.*, 2000, 21, 1113; C. Xiao, K. J. Zhu, *Polym. Int.*, 2001, 50, 414). Storey and Taylor linked a poly($\epsilon$-caprolactone) to form a polyester anhydride with a higher molar mass. The polymer degraded in two stages, thus the rapid hydrolysis of the anhydride bonds was followed by a slower degradation of the poly($\epsilon$-caprolactone) (R. F. Storey, A. E. Taylor, *J. Mol. Sci., Pure Appl. Chem.* 1997, A34, 265). Correspondingly, Korhonen, Helminen and Seppälä prepared polyester anhydrides from prepolymers of poly(c-caprolactone) and polyactide, which anhydrides degraded in two stages (H. Korhonen, J. V. Seppälä, *J. Appl. Polym. Sci.*, 2001, 81, 176; H. Korhonen, A. O. Helminen, J. V. Seppälä, *Macromol. Chem. Phys.*, 2004, 205, 937). Pfeifer, Burdick and Langer have, by using compounds which comprise amines, demonstrated the production of microparticles of lactic acid-based polyester anhydrides and the preparation of the surface. In addition, they have reported the use of microparticles for the transportation of genes (B. A. Pfeifer, J. A. Burdick, and R. Langer, *Biomaterials*, 2005, 26, 117; B. A. Pfeifer, J. A. Burdick, S. R. Little, and R. Langer, *Int. J. Pharm.*, 2005, 34, 210). In the above studies, the polyester anhydrides used were thermoplastic. Furthermore, Helminen, Korhonen and Seppälä have reported the preparation of a cross-linked network-structured polyester anhydride. When using a poly($\epsilon$-caprolactone) prepolymer having a low molar mass, the polyester anhydride was degraded through surface degradation in 48 hours (A. O. Helminen, H. Korhonen, J. V. Seppälä, *J. Pol. Sci., Part A: Pol. Chem.*, 2003, 41, 3788).

In the polymers described above, it is possible to adjust the molar mass and the thermal properties of the polyester being used as the prepolymer. The weakness of the materials in question results from the fact that the hydrophobicity of the prepolymer cannot be adjusted. The purpose of the present invention is to produce novel biodegradable polyester anhydride-based polymers, which differ significantly in their material composition, properties and uses from the polymers presented earlier. The purpose of the present invention is in particular to generate a biodegradable polymer, the decomposition rate of which can be widely adjusted by changing the hydrophobicity of the polymer. Now, this has been unexpectedly realised in the polymers according to the present invention.

BRIEF SUMMARY OF THE INVENTION

The present invention relates to polyester anhydrides, the decomposition rate and mechanism of which are adjustable. In the polymer according to the present invention, a polyester-prepolymer is used to which various ring-structured anhydrides, which have different hydrophobicities, are connected. The prepolymers thus generated are either linked to form linear thermoplastic polyester anhydrides or cross-linked to form network-structured polyester anhydrides.

At the first stage of the production of the polymer according to the present invention, a hydroxy-ended polyester prepolymer is synthetised. The prepolymers can be produced by means of ring-opening polymerisation by using cyclic esters as the monomers. Alternatively, the prepolymers can be produced from hydroxy acids or difunctional monomers by using condensation polymerisation.

As part of the production, it is possible to use different alcohols, which determine the molecular structure of the prepolymer (for instance linear or starshaped) and its molecular size.

At the second stage, the prepolymer is functionalised by using a ring-structured hydrophobic acid anhydride. It is possible to carry out the functionalising either without a catalyst or with a catalyst, such as pyridine. In a polymer according to the present invention, the ring-structured acid anhydride which is used in the functionalising is typically a succinic acid anhydride which comprises an alkenyl chain. When the anhydride reacts with the hydroxy ends of the prepolymer, the ring-structure opens up and forms an acid end. Inventors Bheda J. H. and Moore B. M. used corresponding anhydrides which comprise an alkenyl chain together with polyesters (patent publication WO 2005/076947 A2); similarly, inventors Shalaby S. W. and Schipper E. in the patent publication U.S. Pat. No. 4,388,926A. However, in these patents, the polyester components were not biodegradable and the polyesters described in the patents were not further synthesised to form polyester anhydrides comprising anhydride bonds.

After the functionalising, either linear thermoplastic or cross-linked netlike polyester anhydrides are prepared from the acid-ended prepolymers.

The linear polyester anhydrides can be produced using the methods corresponding to those used in producing the polyanhydrides. Typically, the polyester anhydrides are produced by using a two-stage melt-polycondensation. During the first stage, the acid-ended prepolymer is allowed to react with the acetic acid anhydride, and during the second stage, the actual polycondensation is carried out. The activated prepolymer generated can be purified by using extraction. Alternatively, it is possible to produce polyester anhydrides without a separate purifying stage in the process. In other words, the polycondensation is carried out immediately after the prepolymer has reacted with the acetic acid anhydride. This is advantageous in particular because it avoids sticky prepolymers, which comprise anhydride bonds that are easily hydrolysed.

During the production of cross-linked polyester anhydrides, the acid-ended prepolymer is functionalised so that both an anhydride bond and a vinyl group are generated at the ends of the prepolymer chain. After that, the prepolymer, which comprises a vinyl group, is cross-linked, through the opening up of the double-bond, to a network-structured polyester anhydride. The structure of the prepolymer used can be either linear or branched. The composition, molar mass and molecular structure of the prepolymer can be used to control its viscosity, which makes it possible to choose a suitable crosslinking method for each application. For instance, light-crosslinking at room temperature of prepolymers which have a low viscosity makes it possible to add materials, which are temperature sensitive, to the matrix to be cross-linked.

The present invention is based on the idea that it is possible to adjust the degradation rate of the prepared polymers by adding a hydrophobic component to the prepolymer, preferably a succinic acid anhydride which comprises an alkenyl chain. The hydrophobic component both increases the hydrophobicity of the prepolymer and lowers the glass transition temperature and the melting temperature of the prepolymer. Both of these factors have a significant effect on the degradation behaviour of the polyester anhydride.

It is possible to produce the polymer by connecting, using functionalising, hydrophobic parts, to the structural units, i.e. the polyester blocks, before the polyester blocks are coupled to form polyester anhydrides.

Considerable advantages can be achieved with the present invention. Thus, the polymers according to the present invention are widely applicable to, among others, medical and pharmaceutical applications. Examples of such applications are pharmaceutical ingredients requiring controlled release, and tissue-technology applications. Moreover, such applications of biodegradable polymers may come into question where it is advantageous to adjust the degradation rate of the polymers, or to use polymers which are surface-degradable.

DETAILED DESCRIPTION OF THE INVENTION

Figure 1:
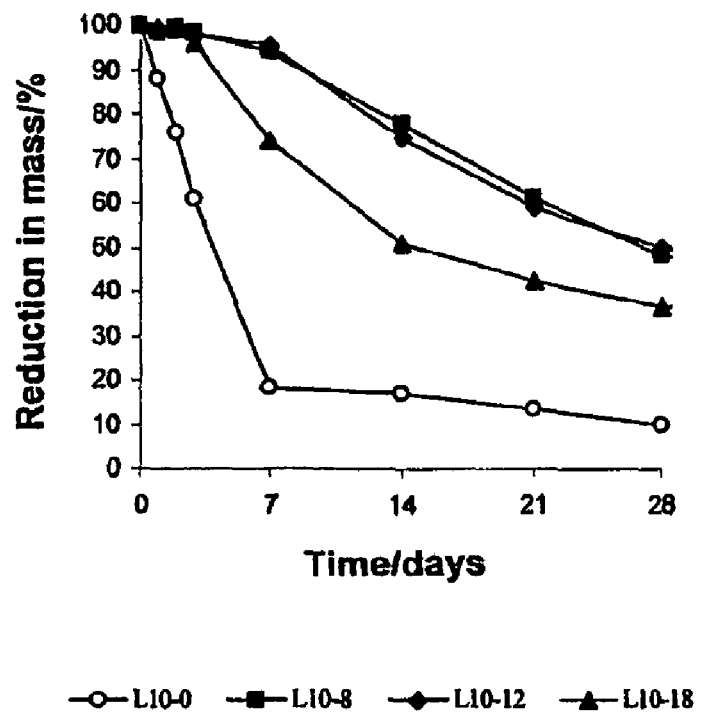
FIG. 1 illustrates reduction in mass during hydrolysis of linear thermoplastic poly(L-lactide)-based polyester anhydrides, according to Example 10, as a function of time.

In the following, the present invention will be examined more closely with the help of a detailed explanation and accompanying examples. The reaction formulas for the preparation of some of the linear and cross-linked polyester anhydrides according to the present invention are as follows:

1. Production of an OH-terminated prepolymer

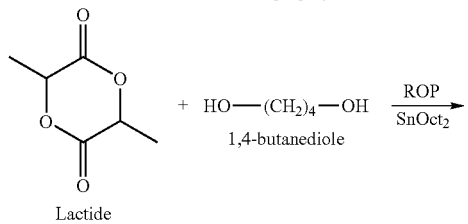

Lactide + HO—(CH$_2$)$_4$—OH  $\xrightarrow[\text{SnOct}_2]{\text{ROP}}$ 1,4-butanediole

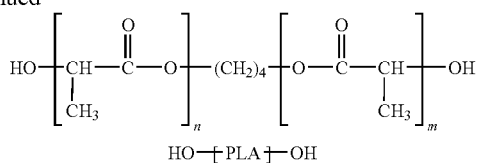
2. Functionalising of an OH-terminated prepolymer to form an acid-terminated prepolymer
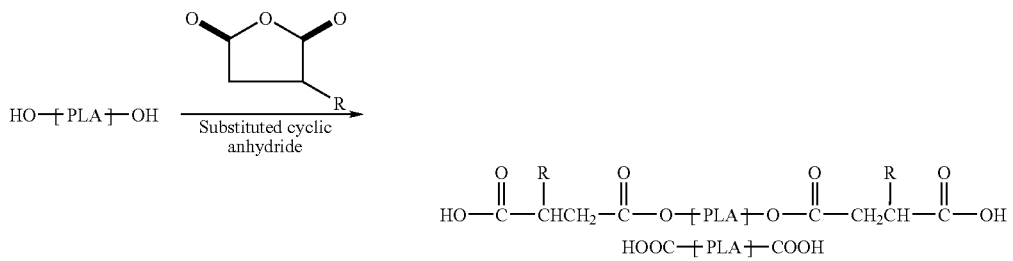
3a. Coupling of acid terminated prepolymer to a linear thermoplastic poly(ester anhydride)
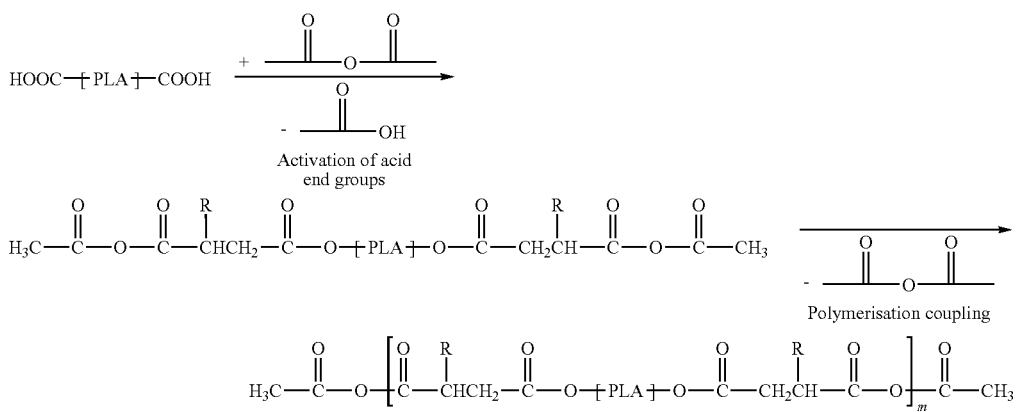
3b. Crosslinking of an acid-terminated prepolymer to form a network-structured polyester anhydride
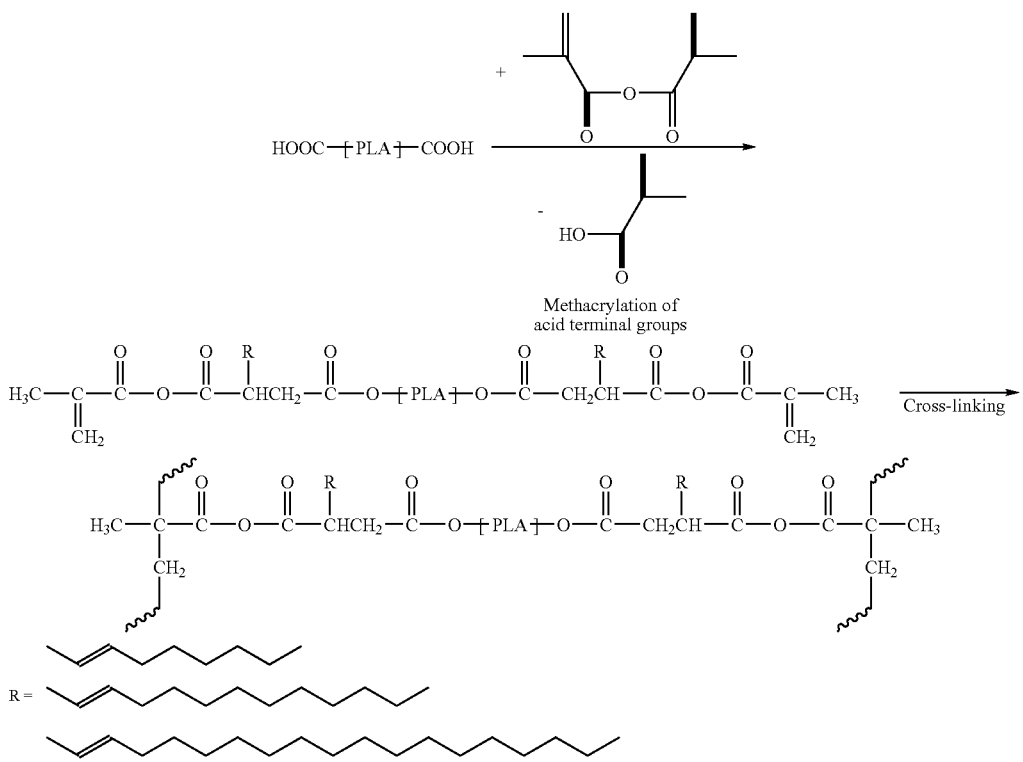

As described above, the thermoplastic or crosslinkable block polymer of a polyester anhydride-type, according to the present invention, comprises and is preferably composed essentially of
 a) polyester blocks,
 b) hydrophobic parts which are connected, by using functionalising, to these polyester blocks, and
 c) anhydride bonds, which couple the functionalised polyester blocks.

In the present invention, an end-functional oligomer, i.e. a telekelic oligomer, is formed, to which oligomer hydrophobic structural parts are connected. Thus, it is not preferable to use (strongly) hydrophobic monomers in the present invention but, instead, to connect hydrophobic parts, which make the product hydrophobic or which increase the hydrophobicity of the product, to the polyester blocks by using functionalising.

Typically, in the block polymers according to the present invention, the polyester blocks are composed of structural units, which are derived from monomers which comprise lactones, aliphatic hydroxy acids or difunctional hydroxyl or carboxylic acid groups, and which units are preferably lactic acids, caprolactones, lactide, glycolide or mixtures of these, not excluding other similar products.

Several generally known methods exist for producing hydroxy-ended prepolymers. Examples of these methods are the ring-opening polymerisation, in the form of either mass or solution polymerisation, and condensation polymerisation. In the polymerisation process, a polymer having a desired molar mass is produced from 1) lactones, hydroxy acids or difunctional monomers, and 2) alcohol (diol or multifunctional alcohol).

In the present invention, examples of the lactones, which are used in the production of the prepolymers, are ε-caprolactone, L-lactide, D-lactide, DL-lactide, glycolide and 1,5-dioxepan-2-one. The hydroxy acid monomers used comprise typically α-hydroxy acids or β-hydroxy acids. The monomer used can be a cyclic carbonate, too, such as trimethyl carbonate. More preferably, aliphatic or aromatic α-hydroxy acid monomers, such as L-lactic acid, D-lactic acid or mixtures of these (so called D,L-lactic acid), glycolic acid, 6-caproylic acid and L- or D-mandelic acid, are used. The hydroxy acid monomers can be multifunctional, too. Examples of these monomers are malic acid and citric acid.

The number of the hydroxy groups of the alcohol which is used in the production of the prepolymer, and the amount of the material used determine the structure (for instance linear or starshaped) and the molecular size of the prepolymer which is generated in the polymerisation. The alcohol to be used is typically multifunctional, such as butanediol, glycol, propane diol, hexane diol, pentaerythritol, dipentaerythritol, mannitol, glycerol or different polyglycerols.

Production of a Hydroxyterminated Prepolymer

In the method according to the present invention, the hydroxyl-terminated prepolymers are produced, according to a preferred embodiment, by using ring-opening polymerisation, from ε-caprolactone, L-lactide or DL-lactide and by using butanediol or pentaerythritol as initiators and tin octoate ($SnOct_2$) as a catalyst. The growth of the polymer takes place from the hydroxyl groups, which means that the butanediol-initiator, which comprises two hydroxyls, forms a linear hydroxyterminated prepolymer, and the pentaerythritol-initiator, which comprises four hydroxyls, forms a starshaped hydroxyterminated prepolymer. The length of the molecular chains, i.e. molar mass of the prepolymer, is adjusted using the molar percentage of the initiator. It is possible to carry out the polymerisation, preferably without using dissolvents, as a mass polymerisation in a liquid state.

In the polymerisation, the initial materials and the catalyst are fed into a preheated reactor, where they are mixed. The air which has been in the reactor after the feeding of the initial materials is flushed with a flow of nitrogen, and thus the reaction takes place in a nitrogen atmosphere. The initial materials are allowed to react for 0.5-6 hours, depending on the temperature (120-180° C.), after which the prepolymers are recovered for later functionalising and analysing.

Production of an Acid-Ended Prepolymer

The second stage according to the present invention comprises functionalising of the hydroxy-ended prepolymer by using a substituted ring-structured anhydride. The ring-structured anhydrides comprise typically substituted succinic acid anhydrides, itaconic acid anhydrides, maleic acid anhydrides, glutaric acid anhydrides, diglycolic acid anhydrides or phthalic acid anhydrides. The substituent can be an alkyl, an alkenyl, an aryl, a cycloalkane or a cycloalkene or a couple of these. Particularly interesting is the succinic acid anhydride, which comprises an alkenyl chain, and which is commercially available in various alkenyl chain lengths. The hydrophobicity of the prepolymer increases as the length of the alkenyl chain increases.

In the method according to the present invention, the carboxylic acid-terminated prepolymers are produced by functionalising the hydroxyl-terminated prepolymers by using succinic acid anhydrides which comprise an alkenyl chain. By using ring-structured acid anhydrides, by-products are avoided. The reactivity of the OH-group of the prepolymer depends on the monomer which is used in the production of the polyester. For instance, when functionalising prepolymers, which are produced from ε-caprolactone, it is possible to use a 0-30 mole % surplus of succinic acid anhydride which is substituted by an alkenyl chain. Correspondingly, when functionalising prepolymers which are prepared from L-lactide or DL-lactide, the surplus of the succinic acid anhydride, which is substituted by an alkenyl chain, is between 50-300 mole %. According to a preferred embodiment, the functionalising of prepolymers of ε-caprolactone is carried out at a temperature of 100-160° C. for a period of 2-6 hours, and the functionalising of prepolymers which are prepared from L-lactide or DL-lactide at a temperature of 100-160° C. for a period of 2-24 hours. If necessary, it is possible to continue the reactions until the degree of functionalising is high enough. After the functionalising, the prepolymers are purified from excess functionalising material by dissolving them first in dichloromethane or a similar dissolvent and then precipitating in hexane, isooctane or similar dissolvents. Finally, the carboxylic acid-ended prepolymers are dried in a vacuum chamber and then stored in a desiccator.

Linking of an Acid-Ended Prepolymer to Form a Linear Thermoplastic Polyester Anhydride The third stage of the production according to the present invention comprises linking, i.e. coupling the carboxylic acid-terminated prepolymer to form a thermoplastic polyester anhydride, or crosslinking it to form a network-structured polyester anhydride. In the production of thermoplastic polyester anhydrides, the oligomeric prepolymers are connected via the anhydride bonds to form a polymer which has a high molar mass and which includes several prepolymer units. The prepolymer to be linked must have a linear structure and comprise two carboxylic acids, through which the anhydride bonds between the prepolymers are formed. It is also possible to use a prepolymer which comprises only one carboxylic acid group, in which case the polymerisation is terminated after this prepolymer has reacted. The termination of the polymerisation is possibly desirable for instance when producing a block copolymer of the ABA type.

Without excluding other polymerisation methods, the most practical method of producing thermoplastic polyester anhydrides is the liquid phase polycondensation. In the liquid phase polycondensation, the polymerisation takes place in two stages. In the first stage, the carboxylic acid groups of the prepolymer are allowed to react with acetic acid anhydride. After that, the actual linking of the prepolymer takes place through polycondensation. The activation of the carboxylic acid groups is carried out by refluxing the prepolymer in acetic acid anhydride, in which case the acid-end reacts and forms an anhydride. Acetic acid is generated as a by-product in the reaction and, because of that, a surplus of acetic acid anhydride is used. It is possible to carry out the reaction by refluxing the prepolymer in acetic acid anhydride, in which case the reaction temperature is the boiling temperature of acetic acid anhydride (140° C.). An adequate reaction time is approximately half an hour.

After the refluxing, the polymerisation can be continued either directly or, alternatively, the prepolymer is purified before the polycondensation. The purifying of the prepolymer is carried out by lowering the temperature to room temperature and then removing most of the excess acetic acid anhydride with the help of vacuum. The final purifying is carried out by extracting the prepolymer in petroleum ether or a similar dissolvent which is suitable for this purpose. In the case of a separate purifying step not being performed, a vacuum is applied immediately after the refluxing in stages in the reactor, in order to remove the excess acetic acid anhydride and the acetic acid which is generated in the reaction. When the acetic acid anhydride and the acetic acid have been removed, the temperature of the reactor is increased to the temperature which is used in the polycondensation.

The actual linking takes place as a polycondensation in the liquid phase. Polycondensation is an equilibrium reaction, in which, in order to advance the polymerisation, the equilibrium must be transferred to the side of the products. The transfer of the equilibrium is carried out by facilitating the removal of the condensation product. This can be done by lowering the pressure and increasing the temperature. Furthermore, in order to remove the condensation product, an inert gas can be fed into the liquid polymer. When the polymerisation advances, the viscosity of the liquid polymer increases significantly, which means that the mixing must be as brisk as possible, in order to allow the condensation product to be removed from the reaction mixture.

The underpressure used in the polycondensation must be considerable, most suitably below 1 mbar. To facilitate advancing of the polymerisation, the temperature should be above 140° C. On the other hand, the highest usable polymeration temperature is limited by the increasing of the side-reactions, which means that it is advantageous to carry out the polymerisation at a temperature below 190° C. A catalyst is not needed in the polycondensation. The time of the polymerisation is approximately one hour to several hours, depending on the temperature used. It is possible to purify the completed polyester anhydride by dissolving it in dichloromethane or another suitable dissolvent, and then precipitating it for instance with hexane or petroleum ether.

Generally, the amount of the linking compound which is used in the coupling of the prepolymer is equimolar or at least essentially equimolar (0.5-2-fold, preferably approximately 0.8-1.2-fold, especially approximately 0.9-1.1-fold) to the functional groups of the prepolymers.

Crosslinking of an Acid-Ended Prepolymer to Form a Network-Structured Polyester Anhydride The crosslinking of an acid-ended prepolymer to form a network-structured polyester anhydride comprises methacrylation of the carboxylic acid-terminated prepolymers by using methacrylic anhydride and crosslinking of these prepolymers through terminal vinyls. It is possible to carry out the crosslinking either using heat or light, or by irradiation, or by employing a combination of these, in a suitable apparatus. The crosslinking can take place before the application or directly in situ.

In the method according to the present invention, and according to a preferred embodiment, when methacrylating carboxylic acid-terminated prepolymers which are produced from $\epsilon$-caprolactone, L-lactide or DL-lactide, a 1.5-5-fold surplus of methacrylic anhydride or a similar double-bonded compound, which forms an anhydride bond, is used. The methacrylation of prepolymers which are produced from $\epsilon$-caprolactone and DL-lactide is carried out at a temperature of 40-100° C. for 6-48 hours. After the functionalising, the prepolymers are purified from the excess functionalising material by dissolving them in dichloromethane and precipitating with hexane or isooctane. Finally, the methacrylated prepolymers are dried in a vacuum chamber and then stored in a freezer.

In a hardening method according to the present invention, the reactions of the double bonds of the prepolymers, i.e. the crosslinking, are initiated, thus producing free radicals in the prepolymer, by using compounds which form radicals, for instance organic peroxide compounds, such as diacyl peroxides, peroxy esters, peroxide carbonates, monoperoxy carbonates, diperoxy ketals, dialkyl peroxides, sulphonyl peroxides, ketone peroxides or peroxy carboxylic acids. The compound which forms radicals can also be dibenzoyl-peroxide, di(2.4-dichlorobenzoyl)peroxide, di-t-butyl peroxide, diacetyl peroxide, dilaurolyl peroxide, didecanonyl peroxide, di-isononanoyl peroxide, succinic acid peroxide, acetyl cyclohexane sulphonyl peroxide, m-chloroperbenzoate acid, tert-butyl perbenzoate, tert-amyl perbenzoate and tert-butyl peroxymaleic acid. In addition, it is possible to use inorganic peroxides, such as hydrogen peroxide, oxygen, ozone, azo compounds, redox-initiators, light-initiators, such as camphor quinine, polymeric peroxides and other ways of forming radicals, or mixtures of these.

In the method according to the present invention, it is possible to accelerate the crosslinking of the prepolymer and to lower the crosslinking temperature by adding more of the accelerator before the crosslinking. For instance, metal compounds, such as cobalt compounds, organic amines, such as dimethyl aminoethyl methacrylate, or other known accelerators, can be used as the accelerators. Accelerators, such as cobalt octoate and cobalt naphtenate and amine accelerators can be used either dissolved in a suitable dissolvent or as such.

In the method according to the present invention, it is possible to adjust the reactions of the double bonds of the prepolymer, i.e. the crosslinking sensitivity and rate, by adding inhibitors after the methacrylation. The inhibitors react with the radicals thus forming inactive molecules. In this way, a premature hardening of the methacrylated prepolymer is prevented and the working time is extended. When the inhibitor has finished working (i.e. has reacted with the radicals), the crosslinking of the prepolymer starts.

In the production of the network-structured biodegradable polyester anhydride, according to the present invention, it is possible to harden the prepolymer by allowing its double bonds to react with each other. In association with the crosslinking, it is possible to use a reactive monomer or macromonomer together with the prepolymer, in which case the double bonds of the separate compounds react with each other, thus forming a network-structured cross-linked polymer. By using a reactive monomer or a reactive macromonomer together with the prepolymer, in the production of the network-structured biodegradable polyester anhydride, it is possible to affect the crosslinking density, to generate flexible, rubbery materials and to decrease the viscosity of the prepolymer.

In the method according to the present invention, the methacrylated prepolymers are cross-linked either thermally by using an initiator, which is sensitive to temperature, or by means of light by using a light initiator. A thermal hardening can be carried out with peroxide at temperatures which are above room temperature, the time of crosslinking varying from a few minutes to 24 hours. Crosslinking using light can be carried out at room temperature, too. The prepolymers which have a low viscosity and which are hardened at room temperature are particularly interesting, because it is possible to add temperature-sensitive materials to them.

The number average molar mass ($M_n$) of the prepolymers (polyester blocks) is generally approximately 750-50,000 g/mole, preferably 1,000-25,000 g/mole, especially approximately 1,500-15,000 g/mole, and, correspondingly, the weight average molar mass ($M_w$) is 800-60,000 g/mole, preferably 1,100-30,000 g/mole, most suitably approximately 1,700-20,000 g/mole. It should be pointed out that the above limits are not restrictive, but, depending on the biodegradation of the product, it is possible to use prepolymers, the molar mass ($M_n$) of which is as much as 100,000-150,000 g/mole and, in turn, the $M_w$ at a corresponding level.

However, according to a more preferable form of application, it is possible to generate prepolymers which have a relatively small molar mass, in which case the molar mass of the prepolymer is most suitably at such a level that the prepolymer is at least essentially plastic.

In the examples below, the $M_w$ was approximately 2,000-7,500 g/mole and the $M_n$ approximately 2,500-8,500 g/mole.

The ratio $M_w/M_n$ (polydispersity) is for instance approximately 1.05-10.0, especially approximately 1.1-5.0, typically approximately 1.1-3.0. It has been found that a narrow molar mass distribution such as this is easy to generate, by using polymerisation methods which are described in more detail below. However, in the present invention, it is possible to use products which have a large polydispersity (PDI even 20).

The polyester anhydrides according to the present invention open up totally new potential applications in the fields of technology, medicine and pharmacy. Broadly speaking, the polyester anhydrides according to the present invention can be applied to biodegradable polymers, in which applications it is advantageous to adjust the degradation rate of the polymers or to use surface-degradable polymers. Not excluding other alternatives, examples of these applications are the use of polymers in tissue technology, either as scaffold-materials or as a polymer-like porosifying agent. Examples of pharmaceutical applications are, in turn, the use of these polymers as matrixes in the release of active ingredients. In this case, surface degradable polyester anhydrides are more preferable, because by using them it is possible to achieve a zero-order release behaviour, and they also enable the release of large molecules. It is possible to add the active material at room temperature, too, which also enables the use of temperature-sensitive active materials. Different composites, too, can be produced from polyester anhydrides, in which case bioactive composites, which include bioceramics such as bioactive glass, are particularly interesting. In surgery, it is possible to use polyester anhydrides for instance in implants and stitch threads.

In the following examples, the present invention is described in more detail.

Example 1

Production of a Linear OH-Ended Polycaprolactone-Based Prepolymer

A two-litre reactor was used, in which the mixing was carried out by two spiral mixers.

First, 200 g of ε-caprolactone (1.75 mole), 8.31 g of 1.4-butanediol (0.092 mole, 5 mole %), and 0.149 g of tin octoate (0.35 mmole, 0.02 mole %), were added into the reactor. After the weighing of the initial materials, a flow of nitrogen was introduced into the reactor for approximately 3 minutes. After introducing the nitrogen, the temperature was raised to 160° C., at which temperature the initial materials were allowed to react for 4 hours. During the polymerisation, the reaction mixture was mixed at a speed of 50 rpm. After the polymerisation, the liquid polymer was cooled and then recovered for a later functionalising. The sample code of the polymer is PCL-BD5-OH. A corresponding prepolymer, having a smaller molar mass (sample code PCL-BD10-OH) was prepared by using 17.56 g of 1.4-butanediol (0.195 mole, 10 mole %).

The molar masses of the polymers thus obtained were determined by using a SEC analysis (Size Exclusion Chromatography) and by comparing them against polystyrene standards. The results showed that the quantity of the 1.4-butanediol controls the molar mass of the prepolymer. The number-average molar mass of the polymer, which comprises 5 mole % of 1.4-butanediol, was 4600 g/mole, and of the polymer, which comprises 10 mole % of 1.4-butanediol, 2400 g/mole. A DSC analysis (Differential Scanning Calorimetry) showed that the prepolymers were partly crystalline when the melting temperatures were 48° C. (PCL-BD5-OH) and 36° C. (PCL-BD10-OH). Peaks, which are characteristic of ester bonds (4.03 ppm) and OH-end functionality (3.61 ppm), were observed in the prepolymer, by using $^1$H-NMR (Nuclear Magnetic Spectroscopy).

Example 2

Production of a Linear OH-Ended Polylactide-Based Prepolymer

The polymerisation was carried out in the same way as in example 1, except that L-lactide or DL-lactide was used as the initial material instead of ε-caprolactide. The amounts of the initial materials were 200 g of L-lactide (1.39 mole), 6.58 g of 1.4-butanediol (0.073 mole, mole %) and 0.118 g of tin octoate (0.02 mole %). The sample code of the polymer was PLLA-BD5-OH. The corresponding prepolymer, although it had a smaller molar mass (sample code PLLA-BD10-OH), was prepared by using 13.89 g of 1.4-butanediol (0.154 mole, 10 mole %). In the poly(DL-lactide)-based polymers, the amounts of DL-lactide used were the same as above (sample codes of the polymers PDLA-BD5-OH and PDLA-BD10-OH).

The molar masses of the polymers obtained were determined by using the SEC analysis and by comparing them against polystyrene standards. The molar masses were at the same level as of the polycaprolactone-based prepolymers in example 1. The number-average molar mass was 5100 g/mole of the polymer PLLA-BD5-OH and 2300 g/mole of the polymer PLLA-BD10-OH. Correspondingly, the number-average molar mass was 4400 g/mole of the polymer PDLA-BD5-OH and 2200 g/mole of the polymer PDLA-BD10-OH. The DSC analysis showed that the prepolymer PLLA-BD5-OH was partly crystalline when the melting temperature was 127° C. and the glass transition temperature was 36° C. The glass transition temperature of the prepolymer PLLA-BD10-OH, which had a smaller molar mass, was 22° C., and no melting peak could be observed. The DL-lactide-based polymers were amorphous and they were observed to have only glass transition temperatures of 30° C. (PDLA-BD5-OH) and 14° C. (PDLA-BD10-OH). By using the $^1$H-NMR method, the prepolymers were observed to have peaks which are characteristic of ester bonds (5.14 ppm) and of OH-end functionality (4.33 ppm).

Example 3

Production of a Star-Shaped OH-Ended Polycaprolactone-Based Prepolymer

The polymeration was carried out in the same way as in example 1, but pentaerythritol, which comprises 4 OH groups, was used instead of the 1.4-butanediol. The amounts of the initial materials were 200 g of ε-caprolactone (1.75 mole), 26.51 g of pentaerythritol (10 mole %) and 0.149 g of tin octoate (0.35 mmole, 0.02 mole %). The sample code of the polymer was PCL-PER10-OH. The preparation of the prepolymer was carried out in a corresponding way, by using 7.5, 5 and 2.5 mole % of pentaerythritol (sample codes PCL-PER7.5-OH, PCL-PER5-OH and PCL-PER2.5-OH).

The molar masses and the melting temperatures were at the same level as for the linear polycaprolactone prepolymers described in example 1. The number average molar mass was 1800 g/mole of the PCL-PER10-OH polymer, 2600 g/mole of the PCL-PER7.5-OH polymer, 3900 g/mole of the PCL-PER5-OH polymer and 7100 g/mole of the PCL-PER2.5-OH polymer. By using the $^1$H-NMR method (nuclear megnetic spectroscopy), the prepolymers were observed to have peaks which are characteristic of ester bonds (4.03 ppm) and of OH-end functionality (3.61 ppm).

Example 4

Functionalising of a Linear OH-Ended Polycaprolactone-Based Prepolymer in Order to Change it from being OH-Ended to being Acid-Ended The functionalising of a prepolymer to change it to being acid-ended was carried out in a 250 ml round-bottom flask using a magnetic rod for the mixing. First, 30 g of the PCL-BD5-OH prepolymer according to example 1 and 5.8 g of (+/−)-2-octen-1-yl succinic acid anhydride (8-SAH) were weighed into the flask. The quantity of the acid anhydride used was 1.3 times greater than the amount of the OH groups of the prepolymer. After the weighing, nitrogen was introduced into the flask, which was then sealed. The flask was placed in a bath of oil at a temperature of 140° C. for 3 hours. The resulting prepolymer was dissolved in dichloromethane and precipitated using hexane. The dissolving and the precipitation were repeated 3 times, in order to remove the excess acid anhydride. To remove the residual dissolvent, the precipitated prepolymer was dried in a vacuum chamber. The functionalisings were carried out in a corresponding way, by using 2-dodecenel-1-yl succinic acid anhydride (12-SAH) or n-octadecenyl succinic acid anhydride (18-SAH), instead of the (+/−)-2-octen-1-yl succinic acid anhydride (8-SAH).

By employing the $^1$H-NMR method, the OH-end functionality in the prepolymers disappeared (the 3.61 ppm peak), and a peak which is characteristic of the generated acid functionality (2.84 ppm) could be observed.

Example 5

Functionalising of a Star-Shaped OH-Ended Polycaprolactone-Based Prepolymer to Change it from being OH-Ended to being Acid-Ended The functionalising of a prepolymer to change it to being acid-ended was carried out in a 250 ml round-bottom flask using a magnetic rod for the mixing. First, 30 g of the star-shaped (four-branched) PCL-PER10-OH prepolymer according to example 3, and 36.85 g of n-octadecenyl succinic acid anhydride (18-SAH) were weighed into the flask. The amount of the anhydride used was equivalent in relation to the amount of the OH-groups of the prepolymer. After the weighing, nitrogen was introduced into the flask, which then was sealed. The flask was placed in a bath of oil at a temperature of 140° C. for 3 hours. The resulting prepolymer was dissolved in dichloromethane and precipitated by using isooctane. The dissolving and the precipitation were repeated 3 times, in order to remove the impurities. To remove the residual dissolvent, the precipitated prepolymer was dried in a vacuum chamber. The functionalisings were carried out in a corresponding way, by using (+/−)-2-octen-1-yl succinic acid anhydride (8-SAH) or 2-dodecenel-1-yl succinic acid anhydride (12-SAH) instead of the n-octadecenyl succinic acid anhydride (18-SAH). Besides isooctane, hexane, too, was used in the precipitations.

By employing the $^1$H-NMR method, the OH-end functionality in the prepolymers disappeared (the 3.61 ppm peak), and a peak which is characteristic of the generated acid functionality (2.84 ppm) could be observed.

Example 6

Functionalising of a Linear OH-Ended Polylactide-Based Prepolymer to Change it from being OH-Ended to being Acid-Ended by Using (+/−)-2-Octen-1-yl Succinic Acid Anhydride (8-SAH)

The functionalising of the linear polylactide-based prepolymer to change it to being acid-ended was carried out in the same way as in example 4, but the amount of the (+/−)-2-octen-1-yl succinic acid anhydride (8-SAH) used was double the amount of the OH-groups in the prepolymer. After the weighing, nitrogen was introduced into the flask, which then was sealed. The flask was placed in a bath of oil at a temperature of 140° C. for 24 hours. The resulting acid-ended prepolymer was dissolved into dichloromethane and precipitated by using hexane. The dissolving and the precipitation were repeated 3 times, by which time the excess acid anhydride had been removed. To remove the residual dissolvent, the precipitated prepolymer was dried in a vacuum chamber.

By employing the $^1$H-NMR method, the OH-end functionality in the prepolymers disappeared (the 3.61 ppm peak), and a peak which is characteristic of the generated acid functionality (2.89 ppm) could be observed.

Example 7

Functionalising of a Linear OH-Ended Polylactide-Based Prepolymer to Change it from being OH-Ended to being Acid-Ended by Using 2-Dodecenel-1-yl Succinic Acid Anhydride (12-SAH)

The functionalising of the linear polylactide-based prepolymer to change it to being acid-ended was carried out in the same way as in example 4, but the amount of the 2-dodecenel-1-yl succinic acid anhydride (12-SAH) used was double the amount of the OH-groups in the prepolymer. After the weighing, nitrogen was introduced into the flask, which was then sealed. The flask was placed in a bath of oil at a temperature of 160° C. for 8 hours. The prepolymer obtained was dissolved in dichloromethane and precipitated by using hexane. The dissolving and the precipitation were repeated 3 times, after which the excess acid anhydride was removed. To remove the residual dissolvent, the precipitated prepolymer was dried in a vacuum chamber.

By employing the $^1$H-NMR method, the OH-end functionality in the prepolymers disappeared (the 3.61 ppm peak), and a peak which is characteristic of the generated acid functionality (2.89 ppm) could be observed.

Example 8

Functionalising of a Linear OH-Ended Polylactide-Based Prepolymer to Change it from being Oh-Ended to being Acid-Ended by Using N-Octadecenyl Succinic Acid Anhydride (18-SAH)

The functionalising of the linear polylactide-based prepolymer to change it to being acid-ended was carried out in the same way as in example 4, but the amount of the n-octadecenyl succinic acid anhydride (18-SAH) used was double the amount of the OH-groups in the prepolymer. After the weighing, nitrogen was introduced into the flask, which then was sealed. The flask was placed in a bath of oil at a temperature of 160° C. for 8 hours. After that, n-octadecenyl succinic acid anhydride was added, if necessary, to produce a total excess of the anhydride 3-fold the amount of the OH-groups of the prepolymer, and the reaction was continued for another 8 hours. The prepolymer obtained was dissolved in dichloromethane and precipitated by using isooctane. The dissolving and the precipitation were repeated 3 times, after which the excess acid anhydride was removed. To remove the residual dissolvent, the precipitated prepolymer was dried in a vacuum chamber.

By employing the $^1$H-NMR method, the OH-end functionality in the prepolymers disappeared (the 3.61 ppm peak), and a peak which is characteristic of the generated acid functionality (2.84 ppm), could be observed.

Example 9

Coupling of an Acid-Ended Polycaprolactone-Based Prepolymer to Form a Thermoplastic Polyester Anhydride The coupling of a prepolymer to form a thermoplastic polyester anhydride was carried out in a 100 ml 3-neck round-bottom flask by using a blade mixer which is rotated by a mixing motor. First, 15 ml of acetic acid anhydride and 15 g of the PCL-BD5-OH prepolymer, which had been functionalised by using the (+/−)-2-octen-1-yl succinic acid anhydride (8-SAH) according to example 4, were weighed into the flask. After the weighing, the flask was placed in a bath of oil, the temperature of which was 130° C. After refluxing for half an hour, an underpressure was carefully introduced into the flask by suction. The excess acetic acid anhydride was removed by increasing for a period of half an hour the underpressure to a final pressure of below 1 mbar. While continuously maintaining this pressure below 1 mbar, the temperature was raised for a period of half an hour to a temperature of 175° C., at which temperature the polycondensation was continued for 1 hour. After the polymerisation, the reaction mixture was cooled rapidly and dissolved in dichloromethane, from which it was precipitated by using hexane. To remove the residual dissolvent, the precipitated polymer was dried in a vacuum chamber. The purified polyester anhydride was stored in a freezer.

The molar mass of the polyester anhydride was determined by using a SEC analysis, and comparing it against polystyrene standards. The number-average molar mass of the prepolymer which was functionalised using the (+/−)-2-octen-1-yl succinic acid anhydride (8-SAH) was 5,100 g/mole, whereas the number average molar mass of the polyester anhydride which was prepared from a prepolymer was 40,000 g/mole.

All the caprolactone-based polyester anhydrides were prepared in a corresponding way. The molar masses and the thermal properties of the caprolactone-based polyester anhydrides are shown in table 1.

TABLE 1

The molar masses and the thermal properties of the caprolactone-based polyester anhydrides.

| 1.4-BD mole % | SAH$^a$ | Prepolymer | | | | Polyester anhydride | | | |
| --- | --- | --- | --- | --- | --- | --- | --- | --- | --- |
| | | $M_n$ g/mole | $M_w$ g/mole | Tg ° C. | Tm ° C. | $M_n$ g/mole | $M_w$ g/mole | Tg ° C. | Tm ° C. |
| 5 | —$^b$ | 4600 | 5500 | — | 48 | | | | |
| 5 | 0 | 5000 | 6700 | — | 50 | 45000 | 99000 | — | 56 |
| 5 | 8 | 5100 | 6400 | — | 33.42$^c$ | 40000 | 82000 | — | 41 |
| 5 | 12 | 5000 | 6500 | — | 32.41$^c$ | 39000 | 78000 | — | 40 |
| 5 | 18 | 5600 | 7000 | — | 30.40$^c$ | — | — | — | — |
| 10 | —$^b$ | 2400 | 2800 | — | 36 | | | | |
| 10 | 0 | 2900 | 3600 | — | 38 | 38000 | 183000 | — | 47 |
| 10 | 8 | 2700 | 3400 | — | 15 | 31000 | 68000 | — | 14 |
| 10 | 12 | 2900 | 3700 | — | 16 | 26000 | 52000 | — | 20 |
| 10 | 18 | 3200 | 4200 | — | 10 | — | — | — | 15 |

$^a$Length of the alkenyl chain of the succinic acid anhydride which is used in the functionalising.
$^b$OH-terminated prepolymer
$^c$Split peak.

Example 10

Coupling of an Acid-Ended Polylactone-Based Prepolymer to Form a Thermoplastic Polyester Anhydride The linking of the polylactide-based prepolymer to form a polyester anhydride was carried out in the same way as in example 9, but instead of the polycapriolactone-based prepolymer, 15 g of a prepolymer which had already been functionalised to make it acid-ended, by using the (+/−)-2-octen-1-yl succinic acid anhydride (8-SAH) according to example 6, and which comprised 5 mole % of 1.4 butanediol, was used as the initial material.

The molar mass of the polyester anhydride was determined by using a SEC analysis, and comparing it against polystyrene standards. The number average molar mass of the PLLA-prepolymer which was described in this example was 4,800 g/mole, whereas the number average molar mass of the polyester anhydride which was prepared from a prepolymer was 22,000 g/mole.

All the polylactide-based polyester anhydrides were prepared in a corresponding way. Their molar masses and thermal properties are shown in table 2.

Example 11

Coupling of Two Acid-Ended Polylactide-Based Prepolymers, which have Different Molar Masses, to Form a Thermoplastic Polyester Anhydride The coupling of the polylactides to form a polyester anhydride was carried out in the same way as in example 9, but instead of a polycaprolactone-based prepolymer, two polylactide prepolymers having different molar masses were used as the initial material. One of the prepolymers was 7.5 g of PLLA-prepolymer comprising 5 mole % 1.4-butanediol, which prepolymer had been functionalised to change it into being acid-ended by using n-octadecenyl succinic acid anhydride (18-SAH), and the other prepolymer used was 7.5 g of PLLA-prepolymer, which had been functionalised to change it into being acid-ended by using n-octadecenyl succinic acid anhydride (18-SAH), and the 1.4-butanediol percentage of which was 10 mole %.

The molar mass of the polyester anhydride was determined by using a SEC analysis, and comparing it against polystyrene standards. The number average molar mass of the PLLA-BD5 prepolymer described in this example was 5,100 g/mole, and for the PLLA-BD10 it was 3,000 g/mole. The number average molar mass of the polyester anhydride which was coupled from the prepolymers was 21,000 g/mole.

Example 12

Methacrylation of a Linear Acid-Ended Polycarprolactone-Based Prepolymer

Functionalising of a linear acid-ended polycarprolactone-based prepolymer, by using methacrylic anhydride, was carried out in a 100 ml round-bottom flask by using a magnetic rod for the mixing. First, 15 g of the acid-ended prepolymer, which had been functionalised by using n-octadecenyl succinic acid anhydride (18-SAH), according to example 4, and approximately a 3-fold excess of methacrylic anhydride (45 g) were weighed into the flask. After the weighing, nitrogen was introduced into the flask, which was sealed. Then, the flask was placed in a bath of oil, the temperature of which was 60° C., for 24 hours. The prepolymer obtained was dissolved into dichloromethane and precipitated by using isooctane. The dissolving and the precipitation were repeated 3 times, after which the methacrylic anhydride excess and the generated by-product, i.e. methacrylic acid, were removed. To remove the residual dissolvent, the precipitated methacrylated prepolymer was dried in a vacuum chamber. The methacrylations were carried out in a corresponding way for the

TABLE 2

The molar masses and the thermal properties of the polylactide-based polyester anhydrides.

| Monom. | 1.4-BD mole % | SAH[a] | Prepolymer $M_n$ g/mole | $M_w$ g/mole | Tg ° C. | Tm ° C. | Polyester anhydride $M_n$ g/mole | $M_w$ g/mole | Tg ° C. | Tm ° C. |
|---|---|---|---|---|---|---|---|---|---|---|
| DLLA | 5 | —[b] | 4400 | 5700 | 30 | — | | | | |
| | 5 | 0 | 4200 | 5600 | 32 | — | 23000 | 39000 | 33 | — |
| | 5 | 8 | 4100 | 5700 | 15 | — | 28000 | 53000 | 23 | — |
| | 5 | 12 | 4000 | 5300 | 8 | — | 18000 | 32000 | 19 | — |
| | 5 | 18 | 4700 | 6100 | 13 | — | 24000 | 49000 | 20 | — |
| DLLA | 10 | —[b] | 2200 | 2700 | 32 | — | | | | |
| | 10 | 0 | 2000 | 2400 | 16 | — | 13000 | 24000 | 20 | — |
| | 10 | 8 | 2300 | 2800 | −10 | — | 19000 | 36000 | 6 | — |
| | 10 | 12 | 2500 | 2900 | −3 | — | 18000 | 32000 | 10 | — |
| | 10 | 18 | 2800 | 3300 | −6 | — | 13000 | 31000 | 10 | — |
| LLA | 5 | —[b] | 5100 | 6200 | 36 | 127 | | | | |
| | 5 | 0 | 4800 | 6000 | 40 | 130 | 27000 | 61000 | 42 | 132 |
| | 5 | 8 | 4800 | 6200 | 20 | 123 | 22000 | 47000 | 36 | 119[c] |
| | 5 | 12 | 4800 | 6200 | 26 | 125 | 25000 | 55000 | 32 | 117[c] |
| | 5 | 18 | 5100 | 6400 | 24 | 126 | 26000 | 81000 | 31 | 121[c] |
| LLA | 10 | —[b] | 2300 | 2900 | 22 | — | | | | |
| | 10 | 0 | 2100 | 2500 | 25 | — | 15000 | 29000 | 32 | — |
| | 10 | 8 | 2500 | 3100 | −7 | — | 21000 | 43000 | 11 | — |
| | 10 | 12 | 2800 | 3300 | −5 | — | 18000 | 33000 | 10 | — |
| | 10 | 18 | 3000 | 3500 | −5 | — | 18000 | 57000 | 11 | — |

[a]Length of the alkenyl chain of the succinic acid anhydride which is used in the functionalising.
[b]OH-terminated prepolymer
[c]The melting temperature in the first heating of the DSC-analysis, no melting peaks appeared in the second heating.

caprolactone-based prepolymers, which had been functionalised by using (+/−)-2-octen-1-yl succinic acid anhydride (8-SAH) or 2-dodecenel-1-yl succinic acid anhydride (12-SAH) instead of the n-octadecenyl succinic acid anhydride (18-SAH). Besides isooctane, hexane, too, was used for the precipitations.

By employing the $^1$H-NMR method, the peak which was characteristic of the acid functionality disappeared (the 2.84 ppm peak), and peaks which are characteristic of the generated double bonds (6.20 ppm and 5.80 ppm) were observed. By employing an infrared spectrometer (FTIR, Fourier Transform Infrared Spectroscopy), characteristic peaks of both double bonds (1634 cm$^{-1}$) and anhydride bonds (1806 cm$^{-1}$) were observed in the prepolymers.

Example 13

Methacrylation of a Starshaped Acid-Ended Polycaprolactone-Based Prepolymer

Functionalising of a starshaped acid-ended polycarprolactone-based prepolymer, by using methacrylic anhydride, was carried out in a 100 ml round-bottom flask and by using a magnetic rod for the mixing. First, 15 g of the acid-ended prepolymer, which had been functionalised by using n-octadecenyl succinic acid anhydride (18-SAH), according to example 5, and approximately a 3-fold excess of methacrylic anhydride (45 g) were weighed into the flask. After the weighing, nitrogen was introduced into the flask, which was sealed. The flask was placed in a bath of oil, the temperature of which was 60° C., for 24 hours. The prepolymer obtained was dissolved into dichloromethane and precipitated by using isooctane. The dissolving and the precipitation were repeated 3 times, after which the excess methacrylic anhydride and the generated by-product, i.e. methacrylic acid, were removed. To remove the residual dissolvent, the precipitated prepolymer was dried in a vacuum chamber. The methacrylations were carried out in a corresponding way for the caprolactone-based prepolymers, which had been functionalised by using (+/−)-2-octen-1-yl succinic acid anhydride (8-SAH) or 2-dodecenel-1-yl succinic acid anhydride (12-SAH) instead of the n-octadecenyl succinic acid anhydride (18-SAH). Besides isooctane, hexane, too, was used for the precipitations.

By employing the $^1$H-NMR method, the peak which was characteristic of the acid functionality disappeared (the 2.84 ppm peak), and peaks which are characteristic of the generated double bonds (6.20 ppm and 5.80 ppm), were observed. By employing the FTIR spectroscopy, characteristic peaks of both double bonds (1634 cm$^{-1}$) and anhydride bonds (1806 cm$^{-1}$) were observed in the prepolymers.

Example 14

Methacrylation of an Acid-Ended Polylactide-Based Prepolymer

Functionalising of an acid-ended polylactide-based prepolymer, by using methacrylic anhydride was carried out in a 100 ml round-bottom flask and by using a magnetic rod for the mixing. First, 15 g of the prepolymer, which had been functionalised by using n-octadecenyl succinic acid anhydride (18-SAH), according to example 8, and approximately a 5-fold excess of methacrylic anhydride (75 g), were weighed into the flask. After the weighing, nitrogen was introduced into the flask, which was sealed. The flask was placed in a bath of oil, the temperature of which was 80° C., for 24 hours. The prepolymer obtained was dissolved into dichloromethane and precipitated by using hexane. The dissolving and the precipitation were repeated 3 times, after which the excess methacrylic anhydride and the generated by-product, i.e. methacrylic acid, were removed. To remove the residual dissolvent, the precipitated prepolymer was dried in a vacuum chamber. The methacrylations were carried out in a corresponding way for the caprolactone-based prepolymers, either if they had been functionalised by using (+/−)-2-octen-1-yl succinic acid anhydride (8-SAH) or 2-dodecenel-1-yl succinic acid anhydride (12-SAH) instead of the n-octadecenyl succinic acid anhydride (18-SAH), or if starshaped polylactide-based prepolymers were used.

By employing the $^1$H-NMR method, the peak which was characteristic of the acid functionality disappeared (the 2.89 ppm peak), and peaks which are characteristic of the generated double bonds (6.20 ppm and 5.80 ppm), were observed.

Example 15

Crosslinking, by Using Heat, of a Methacrylated Linear Polycaprolactone-Based Prepolymer to Form a Network-Structured Polyester Anhydride Approximately 5 g of a linear polycaprolactone-based prepolymer, according to example 12, were weighed in an aluminium mould and melted, if necessary, at a temperature of 40-90° C. Then, 2 weight % of dibenzoyl peroxide was blended into the prepolymer and homogenised by mixing. After that, the prepolymer was poured into a mould and hardened between compression press plates for 1 hour at a temperature of 120° C. When the mould had cooled, the cross-linked polyester anhydride samples were detached and stored in a freezer. The crosslinkings were carried out in the same way as the methacrylated caprolactone-based prepolymers were functionalised by using the (+/−)-2-octen-1-yl succinic acid anhydride (8-SAH) or 2-dodecenel-1-yl succinic acid anhydride (12-SAH) instead of the n-octadecenyl succinic acid anhydride (18-SAH). The degrees of crosslinking, i.e. the gel percentages, were examined gravimetrically by extraction in dichloromethane for 24 hours, and they were between 10-60%. By using FTIR spectroscopy, both the absence of the double bond peak (1634 cm$^{-1}$) and the appearance of the peak which is characteristic of the anhydride bond (1806 cm$^{-1}$) were observed in the cross-linked polyester anhydride.

Example 16

Crosslinking, by Using Heat, of a Methacrylated Starshaped Polycaprolactone-Based Prepolymer to Form a Network-Structured Polyester Anhydride Approximately 5 g of a starshaped polycaprolactone-based prepolymer, according to example 13, were weighed in an aluminium mould and melted, if necessary, at a temperature of 40-90° C. Then, 2 weight % of dibenzoyl peroxide was blended into the prepolymer and homogenised by mixing. After that, the prepolymer was poured into a mould and hardened between compression press plates for 1 hour at a temperature of 120° C. When the mould had cooled, the cross-linked polyester anhydride samples were detached and stored in a freezer. The crosslinkings were carried out correspondingly as the methacrylated caprolactone-based prepolymers were functionalised by using the (+/−)-2-octen-1-yl succinic acid anhydride (8-SAH) or the 2-dodecenel-1-yl succinic acid anhydride (12-SAH) instead of the n-octadecenyl succinic acid anhydride (18-SAH). The degrees of crosslinking, i.e. the gel percentages, were examined gravimetrically by extraction in dichloromethane for 24 hours, and they were above 90%. By using FTIR spectroscopy, both the absence of the double bond peak (1634 cm$^{-1}$, as well as the appearance of the peak which is characteristic of the anhydride bond (1806 cm$^{-1}$), were observed in the cross-linked polyester anhydride.

Example 17

The Reduction in the Mass of a Linear Thermoplastic Polylactide-Based Polyester Anhydride, in a Hydrolysis, as a Function of Time The hydrolysis testings of the polyester anhydrides were carried out by placing the hydrolysis samples in 20 ml test tubes containing 10 ml of a phosphate buffer solution (pH 7.0). The test tubes were placed in a shaker (37° C., 100 rpm). Before the test, the samples, which were disc-shaped, were 2 mm thick and had a diameter of 6 mm. During the hydrolysis, at different points in time, three parallel samples were taken, which were then weighed immediately, after which they were dried. In order to determine the dry weights, the samples were dried in a vacuum chamber for a week. The phosphate buffer was changed once a week. During the hydrolysis, no change of the pH could be observed in the buffer solution.

The reduction in the mass, as a function of time, of the linear thermoplastic poly(L-lactide)-based polyester anhydride, according to example 10, is presented in FIG. 1. As FIG. 1 shows, it is possible to affect the rate of degradation of the polyester anhydride, which rate is generated by using the coupling, by adjusting the hydrophobicity of the cyclic anhydride which is used in the functionalising. The polyester anhydride L10-0 which does not comprise a hydrophobic alkenyl chain degrades almost completely in less than a week, whereas the polyester anhydrides L10-8, L10-12 and L10-18 which comprise alkenyl chains degrade significantly slower. Here, the last number of the codes of the samples (0, 8, 12 or 18) describes the length of the alkenyl chain.

Example 18

The Reduction in the Mass of a Linear Thermoplastic Polyester Anhydride, which Comprises Two Polylactide-Based Prepolymers Having Different Molar Masses, in a Hydrolysis, as a Function of Time The hydrolysis testings of linear thermoplastic polyester anhydrides, according to example 11, which anhydrides comprise two polylactide-based prepolymers having different molar masses, were carried out as described in example 17. Their reduction in the masses during the hydrolysis, as a function of time, is graphically presented in FIG. 2.

Figure 2:
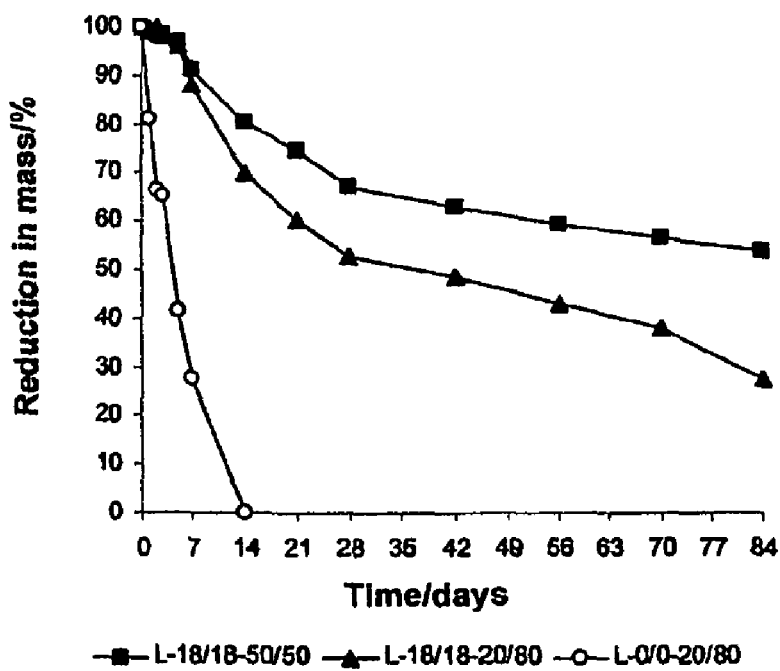
FIG. 2 illustrates reduction in mass during hydrolysis of linear thermoplastic polyester anhydrides comprising two polylactide-based prepolymers having different molar masses, according to Example 11, as a function of time.

As FIG. 2 clearly shows, it is possible to further control the degradation behaviour of the polymer by using prepolymers which degrade at different rates in the production of the polyester anhydride. The degradation slows as the amount of the slowly degrading prepolymer increases. The polymer L-18/18-20/80 comprises two prepolymers (PLLA-BD5-18 and PLLA-BD10-18), which have different molar masses and which thus degrade at different rates, and the ratio between which prepolymers is 20/80 weight %. Correspondingly, in the polymer L-18/18-50/50, the ratio is 50/50 weight % and the polymer degrades more slowly, because in this case the percentage of the prepolymer which degrades more slowly is bigger. As occurs in the case where one prepolymer is used, the alkenyl-chain-free polymer (L-0/0-20/80) degrades significantly faster than the corresponding polymer (L-18/18-20/80) which comprises alkenyl chains.

Example 19

Figure 3:
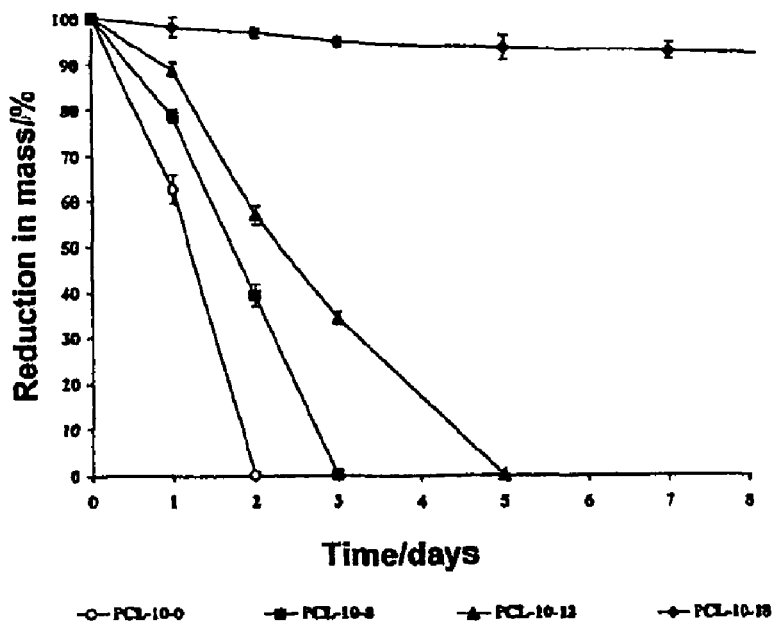
FIG. 3 illustrates reduction in mass during hydrolysis of linear thermoplastic polyester anhydrides which are cross-linked from a linear methacrylated polycaprolactone-based prepolymer, according to Example 15, as a function of time.

The Reduction in the Mass of a Polyester Anhydride, which is Cross-Linked from a Linear Methacrylated Polycaprolactone-Based Prepolymer, in a Hydrolysis, as a Function of Time The hydrolysis testings of polyester anhydrides, which are cross-linked from a linear methacrylated polycaprolactone-based prepolymer, according to example 15, were carried out as described in example 17, and the reduction in the masses of the anhydrides during the hydrolysis, as a function of time, is graphically presented in FIG. 3. As FIG. 3 clearly shows, the increasing of the hydrophobicity by extending the alkenyl chain slows the hydrolytic degradation. The last number of the codes of the degradation curves illustrates the length of the alkenyl chain of the cyclic anhydride which is used in the functionalising of the prepolymer.

Example 20

Figure 4:
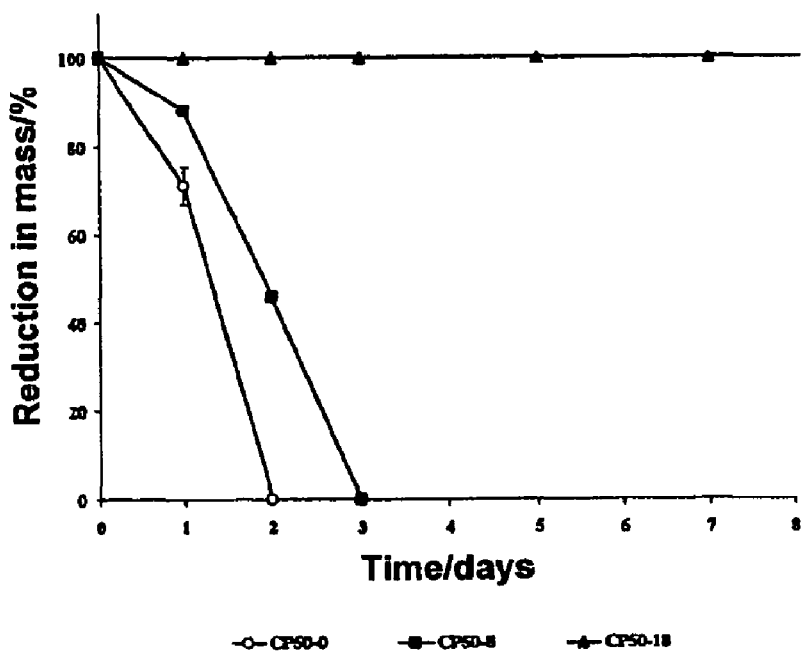
FIG. 4 illustrates reduction in mass during hydrolysis of linear thermoplastic polyester anhydrides which are cross-linked from starshaped prepolymer, according to Example 16, as a function of time.

The Reduction in the Mass of a Polycaprolactone-Based Polyester Anhydride, which is Cross-Linked from a Starshaped Prepolymer, in a Hydrolysis, as a Function of Time The hydrolysis testings of polycaprolactone-based polyester anhydrides, which are cross-linked from starshaped prepolymers, according to example 16, were carried out as described in example 17, and the reduction in the masses of the anhydrides, during the hydrolysis, as a function of time, is graphically presented in FIG. 4. As FIG. 4 clearly shows, again, the increasing of the hydrophobicity by extending the alkenyl chain of the functionalising chemical of the prepolymer clearly slows the hydrolytic degradation. As in FIG. 3, the last number of the code of the degradation curves illustrates the length of the alkenyl chain of the cyclic anhydride which is used in the functionalising of the prepolymer.

Example 21

The Use of the Cross-Linked Polycaprolactone-Based Polyester Anhydride for the Porosifying of the Polymer Matrix A polycaprolactone-based methacrylated prepolymer, which comprises 10 mole % of pentaerythritol and which is functionalised by using (+/−)-2-octen-1-yl succinic acid anhydride (8-SAH), according to example 13, was used as the porosifying material. First, 2 weight % of camphor quinine was added to the prepolymer, after which the prepolymer was cross-linked by using visible light to form a 0.5 mm thick film. In the crosslinking, one side of the film was irradiated first for 10 minutes, after which the film was turned over and the other side was irradiated for 10 minutes. From the cross-linked film, fibres 0.5 mm thick and less than 1 mm wide were cut out.

Figure 5:
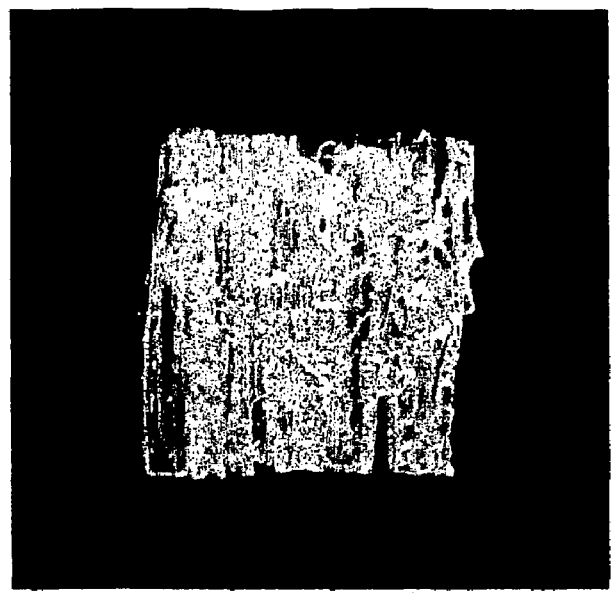
FIG. 5 shows a porosified rod produced in Example 21.

The matrix material to be porosified was a copolymer which comprised 6 mole % of pentaerythritol, the monomer composition of which copolymer was 90 mole % of ε-caprolactone and 10 mole % of DL-lactide, and the hydroxy ends of which were methacrylated by using methacrylic acid anhydride. First, 2 weight % of camphor quinine was mixed into the matrix material and then, 50 weight % of the fibres which are used for porosifying was added into it. From the resulting mixture, which comprised fibres and matrix material, a 2 mm×6 mm×30 mm rod was cross-linked, by using visible light. From the middle of the rod, a piece approximately 1 cm long was cut, which was then placed in a hydrolysis, according to example 17. After 72 hours, the rod was removed from the hydrolysis solution and dried in vacuum. The porosified rod is presented in FIG. 5. As FIG. 5 clearly shows, the porosity in the matrix structure has the form of the hydrolysed fibres.

Example 22

The Use of the Cross-Linked Polycaprolactone-Based Polyester Anhydride for the Release of the Protein A polycaprolactone-based methacrylated prepolymer, which comprises 10 mole % of pentaerythritol and which is functionalised by using (+/−)-2-octen-1-yl succinic acid anhydride (8-SAH), according to example 13, was used for the matrix which comprised protein. A solution-like prepolymer, camphor quinine (2 weight %) and BSA protein (10 weight %, Bovine Serum Album, molar mass 66,400 g/mole) were blended and mixed to form a homogenised mixture. By using visible light, disc-shaped samples, 2 mm thick and having a diameter of 6 mm, were cross-linked from the mixture. Both sides of the sample were cross-linked for 2+4+4 minutes in the irradiation chamber, and cooled between each crosslinking phase.

The hydrolysis testings of the polyester anhydrides, which comprise cross-linked protein, were carried out as in example 17.

UV spectroscopy (Ultra Violet) was used to determine the amount of the BSA released from the hydrolysis solution.

Figure 6:
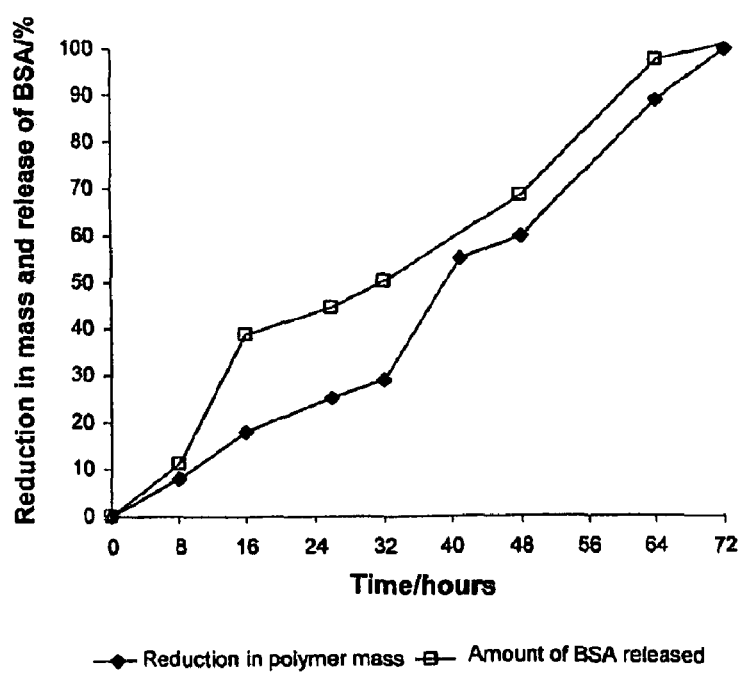
FIG. 6 illustrates reduction in the mass of cross-linked polymer samples, and the amount of BSA released during hydrolysis, according to Example 22, as a function of time.

The reduction in the mass of the cross-linked polymer samples, and the amount of the BSA which was released during the hydrolysis, as a function of time, are graphically presented in FIG. 6. As FIG. 6 shows, the mass of the sample decreases evenly and the amount of the pharmaceutical ingredient released is proportional to the decrease in the mass. In this case, the behaviour of the degradation and the release is typical of surface-erodible polymers.

Example 23

The Use of the Cross-Linked Polycaprolactone-Based Polyester Anhydride for the Release of the Macromolecule Polycaprolactone-based methacrylated prepolymer which comprises 10 mole % of pentaerythritol, which is functionalised by using (+/−)-2-octen-1-yl succinic acid anhydride (8-SAH), according to example 13, was used for the matrix which comprises dextrane. The material used for comparison was a polymer, in which carboxylic acid anhydride (O-SAH) was used as the functionalising material instead of the (+/−)-2-octen-1-yl succinic acid anhydride (8-SAH). The solution-like prepolymer, camphor quinine (2 weight %) and dextrane (10 weight %, molar mass 2,000,000 g/mole) were blended and homogenised by mixing. Samples, 2 mm thick and having a diameter of 6 mm, were taken from the mixture and cross-linked using visible light. The time for the crosslinking for both sides of the samples was 2+4+4 minutes in the irradiation chamber, and cooling was carried out between each crosslinking phase.

Figure 7:
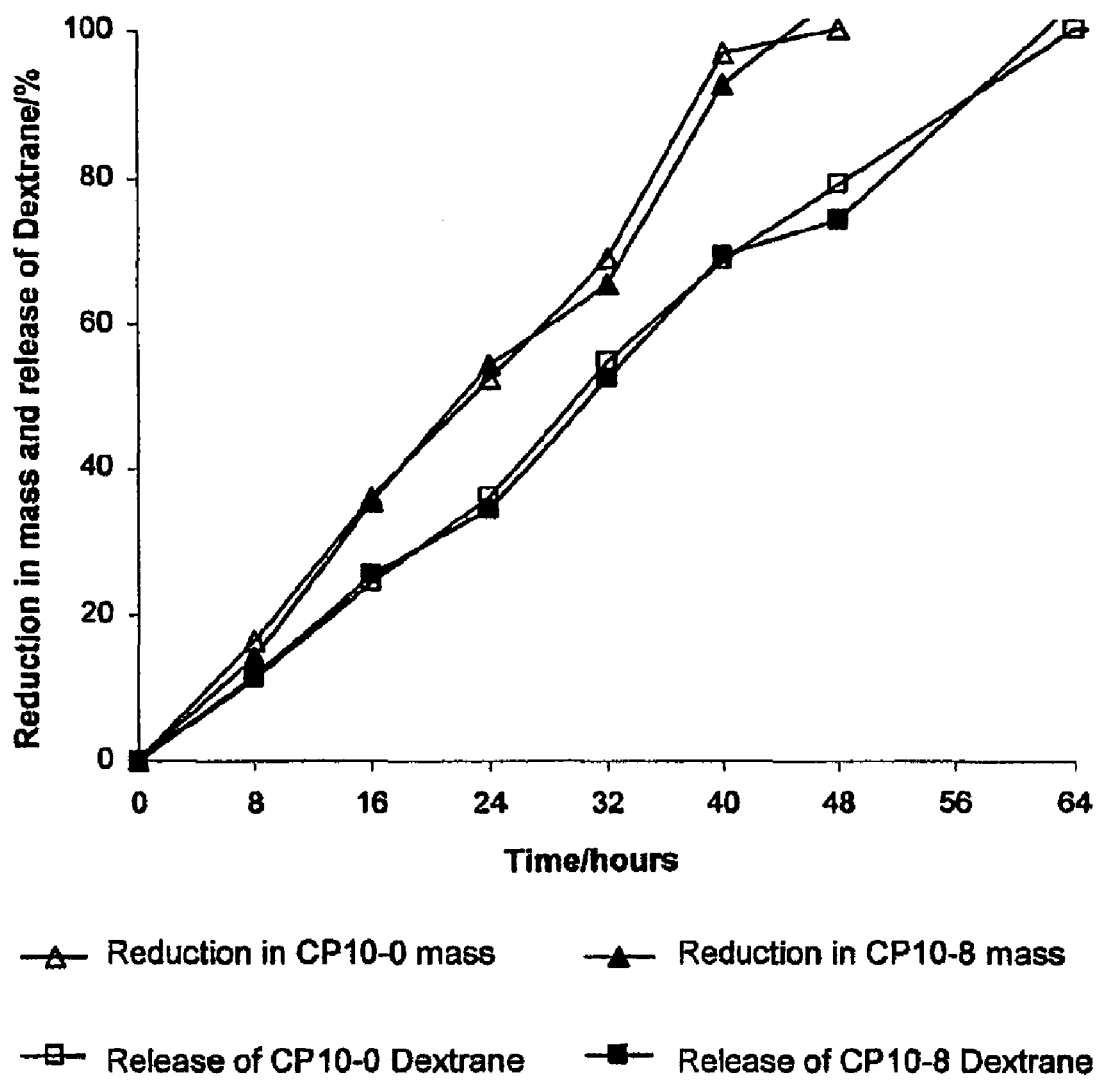
FIG. 7 illustrates reduction in the mass of cross-linked polymer samples, and quantity of released dextrane during hydrolysis, according to Example 23, as a function of time.

The hydrolysis testings of the cross-linked dextrane-bearing polyester anhydrides were carried out as in example 17. The quantity of the released dextrane was determined from the hydrolysis solution by using gel filtration chromatography. The reduction in the mass of the cross-linked polymer samples and the quantity of the released dextrane during the hydrolysis as a function of time, are shown in FIG. 7. As FIG. 7 shows, the mass of the sample decreases evenly and the quantity of the dextrane released is proportional to the decrease in the mass. In this case, the behaviour of the degradation and the release is typical of surface-erodible polymers. In addition, FIG. 7 shows that the polymer which is functionalised using the (+/−)-2-octen-1-yl succinic acid anhydride (8-SAH), i.e. the more hydrophobic polymer, is degraded more slowly.

The invention claimed is:

1. A poly(ester) anhydride, said poly(ester) anhydride comprising the reaction product of:

an acid-terminated prepolymer and an acid anhydride, said acid-terminated prepolymer comprising the reaction product of:

hydroxy-terminated polyester prepolymer comprising two or more hydroxy groups; and a ring-structured substituted anhydride, wherein said substituent(s) is/are selected from an alkyl, alkenyl, aryl, cycloalkane and cycloalkene group.

2. A poly(ester) anhydride, said poly(ester) anhydride comprising the reaction product of:

an acid-terminated prepolymer; and an acid anhydride, said acid-terminated prepolymer having the formula

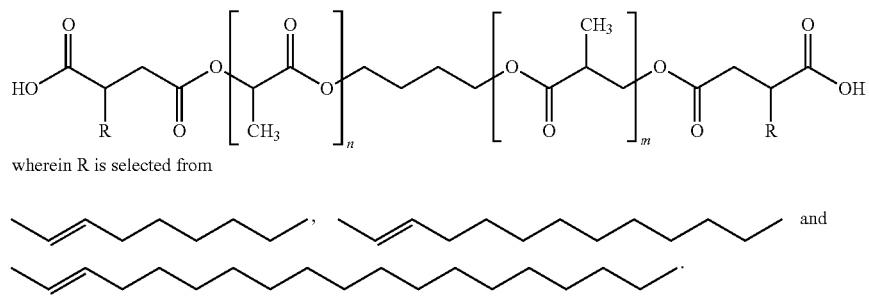

wherein R is selected from

3. The poly(ester) anhydride according to claim 1 wherein the acid anhydride is acetic anhydride.

4. The poly(ester) anhydride according to claim 1 wherein the acid anhydride is methacrylic acrylic acid anhydride.

5. The poly(ester) anhydride according to claim 2 wherein the acid anhydride is acetic anhydride.

6. The poly(ester) anhydride according to claim 2 wherein the acid anhydride is methacrylic acrylic acid anhydride.

* * * * *